(12) United States Patent
Stanjek

(10) Patent No.: US 9,914,744 B2
(45) Date of Patent: Mar. 13, 2018

(54) METHOD FOR PRODUCING CARBAMATOORGANOSILANES

(71) Applicant: Wacker Chemie AG, Munich (DE)

(72) Inventor: Volker Stanjek, Ampfing (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/023,374

(22) PCT Filed: Sep. 17, 2014

(86) PCT No.: PCT/EP2014/069818
§ 371 (c)(1),
(2) Date: Mar. 19, 2016

(87) PCT Pub. No.: WO2015/040070
PCT Pub. Date: Mar. 26, 2015

(65) Prior Publication Data
US 2016/0200745 A1    Jul. 14, 2016

(30) Foreign Application Priority Data
Sep. 20, 2013   (DE) .................. 10 2013 218 972

(51) Int. Cl.
*C07F 7/02*   (2006.01)
*C07F 7/18*   (2006.01)

(52) U.S. Cl.
CPC .......... *C07F 7/1892* (2013.01); *C07F 7/1836* (2013.01)

(58) Field of Classification Search
CPC .................................. C07F 7/1892
USPC .................................. 556/420
See application file for complete search history.

(56) References Cited

U.S. PATENT DOCUMENTS

| 5,220,047 A | 6/1993 | Pohl et al. |
| 6,673,954 B1 * | 1/2004 | Gedon ............ C07F 7/1892 556/420 |
| 2010/0069656 A1 | 3/2010 | Stanjek et al. |

FOREIGN PATENT DOCUMENTS

| EP | 0 583 581 A1 | 2/1994 |
| EP | 2 097 426 B1 | 9/2009 |
| WO | 01/00634 A1 | 1/2001 |
| WO | 2007/037817 A2 | 4/2007 |

* cited by examiner

*Primary Examiner* — Sudhakar Katakam
*Assistant Examiner* — Kofi Adzamli
(74) *Attorney, Agent, or Firm* — Brooks Kushman P.C.

(57) ABSTRACT

Carbamatoorganosilanes are produced in exceptionally high yield with a high degree of purity, by reacting an aminoorganosilane with a dialkylcarbonate in the presence of a basic catalyst, wherein a first reaction period proceeds at a temperature in the range of 35-65° C., followed by a later reaction period at a temperature at least 10° C. higher. A low level of catalyst allows its removal by simple exit filtration, without a separate filtration step.

13 Claims, No Drawings

METHOD FOR PRODUCING CARBAMATOORGANOSILANES

CROSS REFERENCE TO RELATED APPLICATIONS

This application is the U.S. National Phase of PCT Appln. No. PCT/EP2014/069818 filed Sep. 17, 2014, which claims priority to German Application No. 10 2013 218 972.9 filed Sep. 20, 2013, the disclosures of which are incorporated in their entirety by reference herein.

BACKGROUND OF THE INVENTION

1. Field of the Invention

The invention relates to a process for preparing carbamatoorganosilanes from corresponding aminoorganosilanes and dialkyl carbonate.

2. Description of the Related Art

Various processes for preparing 3-carbamatopropylsilanes of the formula (1) are known from the prior art.

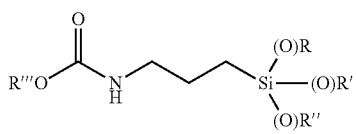
(1)

Preparative processes customarily employed usually start out from 3-aminopropylsilanes of the formula (2) and these are reacted with dialkyl carbonates with elimination of an alcohol to form the product. Said processes are described, for example, in EP 0 583 581, U.S. Pat. No. 6,673,954 or WO 2007/037817.

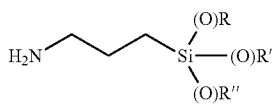
(2)

However, the processes as described in the prior art have a number of disadvantages. Firstly, comparatively large amounts (>0.25%) of a basic metal alkoxide are used as catalyst. These have to be neutralized before the crude product mixture is worked up, and the metal salts formed here make an additional filtration step necessary. It would therefore be desirable to reduce the amount of catalyst to a minimum, ideally to such an extent that, in an industrial process, it is sufficient to drain off the fully worked up product mixture through a simple filter unit in the reactor outlet. Such "police filters", which remove very small amounts of possible suspended materials from a reaction product, are prior art and are present in most industrial production plants.

A further disadvantage of the processes described in the prior art lies in either moderate yields of 78-92% (U.S. Pat. No. 6,673,954) or relatively large amounts (about 2%) of unreacted aminosilanes (EP 0 583 581). Here, unreacted aminosilanes, in particular, represent a great problem since firstly they can be removed only with difficulty from the product and secondly they react, in the most important application of carbamatosilanes, viz. use for the synthesis of the corresponding isocyanatosilanes, with the latter, which leads to urea by-products, biuret by-products or even oligomeric or polymeric by-products.

It would therefore be desirable to have a process which no longer has these disadvantages.

SUMMARY OF THE INVENTION

The invention provides a process for preparing carbamatoorganosilanes (CS) of the general formula (3),

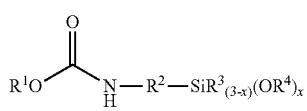
(3)

wherein an aminoorganosilane (AS) of the general formula (4), $$NH_2-R^2-SiR^3_{(3-x)}(OR^4)_x \qquad (4)$$

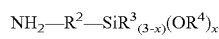

is reacted with a dialkyl carbonate (DAC) of the general formula (5),

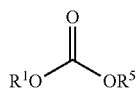
(5)

in the presence of a basic catalyst (K), where
$R^1$, $R^3$, $R^4$ and $R^5$ can be identical or different and are each a monovalent, unsubstituted or substituted hydrocarbon radical,
$R^2$ is a divalent, unsubstituted or substituted hydrocarbon radical and
x is 1, 2 or 3,
and during the reaction there is a period (P1) in which the reaction temperature is in a range from 35 to 80° C. for a time of at least 30 minutes and there is a later reaction period (P2) in which the reaction temperature is at least 10° C. higher than during the period (P1).

DETAILED DESCRIPTION OF THE PREFERRED EMBODIMENTS

The invention is based on the completely surprising discovery that the reaction rate can be increased only to a very limited extent by higher reaction temperatures, especially at the preferred relatively low catalyst contents. On the contrary, it was found that the reaction ceases virtually completely when the reaction temperature is at excessively high temperatures for a relatively long period of time.

On the other hand, it was found that the reaction becomes very slow at low reaction temperatures, especially toward the end of the reaction.

This surprising discovery leads to the dilemma that either it is necessary to use relatively high catalyst concentrations or, in the case of a relatively high reaction temperature, only an incomplete conversion is achieved or, in the case of a relatively low reaction temperature, very long reaction times are required. None of these three alternatives is desirable.

The process of the invention solves this dilemma by large parts of the reaction being carried out during a first period in a relatively low temperature range, followed by a second period having a higher temperature during which the reaction is completed, even before the reaction ceases due to the higher reaction temperature.

In the process of the invention, the reaction product mixture preferably has a residual content of aminoorganosilane (AS) of less than 1 mol %, more preferably less than 0.5 mol %, and in particular less than 0.3 mol %, based on the total content of aminoorganosilane (AS) and carbamatoorganosilanes (CS), at the end of the reaction.

Examples of radicals $R^1$ are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical, isooctyl radicals and the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; alkenyl radicals such as the vinyl, 1-propenyl and 2-propenyl radicals; aryl radicals such as the phenyl, naphthyl, anthryl and phenanthryl radicals; alkaryl radicals such as the o-, m-, and p-tolyl radicals; xylyl radicals and ethylphenyl radicals; and aralkyl radicals such as the benzyl radical, and the α- and β-phenylethyl radicals.

Examples of substituted radicals $R^1$ are haloalkyl radicals such as the 3,3,3-trifluoro-n-propyl radical, the 2,2,2,2',2', 2'-hexafluoroisopropyl radical and the heptafluoroisopropyl radical and haloaryl radicals such as the o-, m- and p-chlorophenyl radicals.

The radical $R^1$ is preferably an unsubstituted or halogen-substituted, monovalent hydrocarbon radical having from 1 to 6 carbon atoms, more preferably an alkyl radical having 1 or 4 carbon atoms, and in particular the ethyl or methyl radical.

Examples of radicals $R^5$ are the radicals indicated for $R^1$. The radical $R^5$ is preferably an unsubstituted or halogen-substituted monovalent hydrocarbon radical having from 1 to 6 carbon atoms, more preferably an alkyl radical having 1 or 4 carbon atoms, and in particular the ethyl or methyl radical.

$R^1$ and $R^5$ are most preferably identical, with particular preference being given to both $R^1$ and $R^5$ each being ethyl radicals or else each being methyl radicals.

Examples of radicals $R^4$ are, independently of one another, the radicals indicated for $R^1$.

The radicals $R^4$ are preferably each an unsubstituted or halogen-substituted, monovalent hydrocarbon radical having from 1 to 6 carbon atoms, more preferably an alkyl radical having from 1 to 4 carbon atoms, and in particular the ethyl or methyl radical.

Particular preference is given to all radicals $R^4$, the radical $R^1$ and the radical $R^5$ being identical, with particular preference being given to all these radicals each being either ethyl radicals or else each being methyl radicals.

Examples of radicals $R^3$ are the radicals indicated for $R^1$. The radical $R^3$ is preferably an unsubstituted or halogen-substituted, monovalent hydrocarbon radical having from 1 to 6 carbon atoms, more preferably an alkyl radical having 1 or 4 carbon atoms, and in particular the methyl radical.

Examples of radicals $R^2$ are divalent alkylene radicals having from 1 to 20 carbon atoms, e.g. the methylene, ethylene, n-propylene, butylene, pentylene, hexylene, heptylene, octylene, nonylene or n-decylene radicals. The radicals mentioned can also have further alkyl substituents such as methyl, ethyl or propyl substituents. Halogen substituents, e.g. chlorine or bromine substituents are also possible. In addition, the radicals $R^2$ can also be divalent cyclic radicals, e.g. cyclopentylene, cyclohexylene or phenyl radicals. These, too, can have the abovementioned alkyl or halogen substituents.

The radicals $R^2$ are preferably alkylene radicals having from 1 to 6 carbon atoms, more preferably the butylene, 2-methylpropylene, propylene and methylene radicals, in particular the propylene and methylene radicals.

The variable x is preferably 2 or 3.

The temperature during the earlier reaction period (P1) is preferably at least 40° C., more preferably at least 45° C., and in particular at least 50° C. The temperature during the earlier reaction period (P1) is preferably not more than 75° C., more preferably not more than 70° C., and in particular not more than 65° C.

The temperature during the later reaction period (P2) is preferably at least 15° C. higher, more preferably at least 20° C. higher, than in the earlier period (P1). The preferred temperature range during the second period (P2) is from 70 to 130° C., in particular from 70 to 100° C.

The components aminosilane (AS), dialkyl carbonate (DAC) and catalyst (K) are preferably combined in their entirety before or during the first reaction period (P1). The period (P1) preferably continues for at least 30 additional minutes, more preferably at least 45 additional minutes, after the complete addition of all components before the reaction mixture is heated and the period (P2) commences.

Preferred examples of carbamatosilanes (CS) of the general formula (3) are N-(3-trimethoxysilylpropyl)-O-methylcarbamate, N-(3-triethoxysilylpropyl)-O-ethylcarbamate, N-(3-methyldimethoxysilylpropyl)-O-methylcarbamate, N-(3-methyldiethoxysilylpropyl)-O-ethylcarbamate, N-(trimethoxysilylmethyl)-O-methylcarbamate, N-(triethoxy-silylmethyl)-O-ethylcarbamate, N-(methyldimethoxysilylmethyl)-O-methylcarbamate and N-(methyldiethoxysilylmethyl)-O-ethylcarbamate, in particular N-(3-trimethoxysilylpropyl)-O-methylcarbamate, N-(3-triethoxysilylpropyl)-O-ethylcarbamate, N-(trimethoxysilylmethyl)-O-methylcarbamate, N-(triethoxysilylmethyl)-O-ethylcarbamate and N-(methyldimethoxysilylmethyl)-O-methylcarbamate.

These preferred carbamatosilanes (CS) are preferably prepared from aminosilanes (AS) of the general formula (4) and dialkyl carbonates (DAC) of the general formula (5) which have precisely the same radicals $R^1$ to $R^4$ and the same variable x as the carbamatosilane (CS) obtained. The radical $R^5$ in the dialkyl carbonate (DAC) is preferably the same as the radical $R^1$.

In the reaction according to the invention, the aminosilanes (AS) and the dialkyl carbonates (DAC) are preferably used in a ratio of from 1.0:0.9 to 1.0:3.0, more preferably in a ratio of from 1.0:1.0 to 1.0:2.0, in particular in a ratio of from 1.0:1.0 to 1.0:1.5. To achieve very complete conversion of the aminosilane component (AS) but also achieve a very good space-time yield, i.e. to use a very small excess of dialkyl carbonate (DAC), a ratio of aminosilane (AS) to dialkyl carbonate (DAC) of from 1:1.1 to 1:1.4 represents a particularly preferred optimum.

Both the appropriate aminosilanes (AS) and the dialkyl carbonates (DAC) are commercially available in large quantities from numerous different suppliers.

As catalyst (K), preference is given to using metal alkoxides, in particular alkali metal or alkaline earth metal alkoxides. Particularly preferred catalysts are sodium methoxide, sodium ethoxide, potassium methoxide, potassium ethoxide, calcium methoxide and calcium ethoxide. In a particularly preferred embodiment of the invention, an alkoxide whose alkyl group corresponds to the radicals $R^4$ in the formula (3) is used. This is advantageous especially when all radicals $R^1$, $R^4$ and $R^5$ are identical.

The catalyst can be used as such or else in the form of a solution, in particular in the form of an alcoholic solution. In the case of an alcoholic solution, the alkyl groups of the alcohol and of the alkoxide are preferably identical. Suitable catalyst solutions which typically have a concentration of 10-330 of the metal alkoxide in the corresponding alcohol are commercially available and are more preferably used because of their easy meterability.

The content of the catalyst (K) is preferably not more than 0.2% by weight, more preferably not more than 0.19% by weight, and in particular not more than 0.15% by weight, in each case based on the weight of the total reaction mixture.

Apart from the components aminosilane (AS), dialkyl carbonate (DAC) and catalyst (K), the reaction mixture preferably contains further materials such as solvents in amounts of not more than 50% by weight, more preferably not more than 30% by weight, and in particular not more than 15% by weight, in each case based on the total reaction mixture. In a particularly preferred process variant, the reaction mixture contains no further components, in particular no further solvents, in addition to the reactants and the catalyst (K) and any solvent in which the catalyst (K) was dissolved.

After the end of the reaction, the reaction mixture is preferably neutralized by addition of an acid. The acid can in principle be any acid. Examples are organic acids, in particular carboxylic acids such as formic acid, acetic acid, propionic acid, butyric acid, citric acid, oxalic acid, tartaric acid, benzoic acid, ammonium acetate, ammonium formate, or else alkylammonium compounds such as triethylammonium chloride, likewise inorganic acids such as hydrochloric acid, sulfuric acid, phosphoric acid, partially esterified sulfuric or phosphoric acid, toluenesulfonic acid, nitric acid or else ammonium compounds such as ammonium sulfate, or ammonium chloride. Preference is given to using anhydrous acids.

The acid is preferably added in such an amount that from 0.8 to 10 mol, particularly preferably from 0.9 to 2 mol, in particular from 0.99 to 1.5 mol, of acid functions are present per 1 mol of basic functions in the catalyst (K).

In a preferred embodiment of the invention, the acid is added in such an amount that the pH of the reaction mixture just changes, depending on the acid used, from strongly alkaline to acidic, weakly acidic, neutral or weakly basic. The pH can, for example, be determined by means of a pH electrode or else by bringing a sample of the reaction mixture into contact with a moistened pH paper.

The neutralization can be carried out either at room temperature or at elevated temperatures. In a particularly preferred process, the neutralization is carried out immediately after the end of the reaction without the reaction mixture being heated or cooled to an appreciable extent, i.e. by more than 10° C. In an industrial process, this has the advantage that no additional times are required for heating and cooling operations. The subsequent removal of the low boilers (see below) by distillation can also be commenced immediately subsequently without any appreciable heating or cooling steps, i.e. temperature changes of more than 10° C.

The preferably solid neutralization product from the catalyst is preferably removed by means of a filtration step. In a particularly preferred embodiment of the invention, the amount of the catalyst salt is so small that this filtration is unproblematical, e.g. it is not carried out in the form of a separate filtration step but instead the reaction mixture is merely drained from the reaction vessel through a filter installed in the pipe.

The alcohol liberated in the reaction and also any excess of dialkyl carbonate (DAC) used are preferably removed by distillation. This can be carried immediately after the reaction by the low boilers to be removed being distilled off directly from the reaction mixture, but can also be carried out in a separate distillation step, e.g. by means of a thin film evaporator or falling film evaporator. The distillation can also be carried out in the presence of the neutralized but not yet removed catalyst (K).

The process of the invention can be carried out both batchwise and continuously. This applies both to the actual reaction and also to the work-up steps described. It is likewise conceivable for only individual process steps to be carried out continuously, e.g. for the reaction to be carried out continuously but the work-up to be carried out batchwise. Conversely, it is also of course possible to carry out the reaction batchwise, while subsequent work-up steps, in particular the removal of the low boilers by distillation, are carried out continuously.

The process of the invention has the advantage that the carbamatosilane (CS) is, even without further purification steps, obtained in a high purity of preferably >95%, in particular >97%.

The process of the invention has the advantage that it gives very good space-time yields and is thus inexpensive.

The process of the invention has the advantage that it makes do with the very low catalyst contents indicated, which makes the removal of the neutralized, usually solid and salt-like catalyst very easy.

The process of the invention has the advantage that it leads to very high conversions and very low residual contents of unreacted aminosilane (AS).

The process of the invention has the advantage that it is very simple and robust.

The carbamatosilane (CS) prepared by the process of the invention can, without further purification steps, be used in moisture-curing systems, e.g. in silane-crosslinking adhesives and sealants, as water scavenger and/or bonding agent.

A preferred use of the carbamatosilane (CS) prepared by the process of the invention is further processing to form corresponding isocyanatosilanes. This is usually carried out by means of thermal dissociation of the carbamate group to give the respective isocyanate and methanol. Suitable processes are described, inter alia, in EP 2 097 426.

All the above symbols in the above formulae have their meanings independently of one another in each case. In all formulae, the silicon atom is tetravalent.

In the following examples, all amounts and percentages are by weight, all pressures are 0.10 MPa (abs.) and all temperatures are 20° C. unless indicated otherwise in the particular case.

Example 1

Process According to the Invention for Preparing N-(3-trimethoxysilylpropyl)-O-methylcarbamate A mixture of 275.1 g (3.054 mol) of dimethylcarbonate and 3.14 g of a 30% strength solution of sodium methoxide in methanol (corresponds to 0.94 g of pure sodium methoxide) is placed in a 1 l four-neck flask provided with dropping funnel, Liebig condenser, precision glass stirrer and thermometer and heated to 55° C. At this temperature, 456.3 g (2.545 mol) of aminopropyltrimethoxysilane are added over a period of 30 minutes. To maintain the temperature, slight cooling is necessary.

The mixture is subsequently stirred at 55° C. for a further one hour and is then heated to 80° C. At this temperature, the mixture is stirred for a further two hours.

Finally, 1.15 g of acetic acid are added. A drop taken from the reaction mixture is placed on a previously moistened pH paper. The Reaction mixture displays a pH of from 5 to 6.

The low boilers are removed from the neutralized reaction mixture by distillation. For this purpose, the pressure is reduced in steps to down to 1 mbar, while the temperature at the bottom firstly remains at 80° C. and is finally increased to 110° C. The distillation is concluded as soon as no more distillate goes over. Analysis of the distillate by means of GC and/or $^1$H-NMR shows that the distillate consists virtually exclusively (i.e. to an extent of more than 99%) of the methanol liberated and the dimethyl carbonate which has been used in excess.

A pale yellow product is obtained in a purity of 98.4%. The yield is virtually quantitative (>99%) based on the aminosilane used.

During the reaction, small samples (<5 ml) are taken at the end of the subsequent stirring time at 55° C., after one hour of further stirring at 80° C. and at the end of the reaction, i.e. after two hours of further stirring at 80° C., neutralized with acetic acid, with the pH being monitored (see above) by means of previously moistened pH paper, and measured by means of $^1$H-NMR. The residual contents of unreacted aminosilane determined here are shown in Table 1.

(Remark: After addition of the acetic acid, the aminosilane is present in partially protonated form)

Example 2

Process According to the Invention for Preparing N-(3-Tri-Methoxysilylpropyl)-O-Methylcarbamate The procedure of Example 1 is repeated, but this time a mixture of 456.3 g (2.545 mol) of aminopropyltrimethoxysilane and 3.14 g of a 30% strength by weight solution of sodium methoxide in methanol (corresponds to 0.94 g of pure sodium methoxide) is placed in the reaction vessel and heated to 55° C. At this temperature, 275.1 g (3.054 mol) of dimethyl carbonate are introduced over a period of 30 minutes. To maintain the temperature, slight cooling is necessary.

The remainder of the experiment is carried out exactly as described in Example 1.

A pale yellow product is obtained in a purity of 98.6%. The yield is virtually quantitative (>99%) based on the aminosilane used.

During the reaction, small samples (<5 ml) again are taken at the end of the subsequent stirring time at 55° C., after one hour of further stirring at 80° C. and at the end of the reaction, i.e. after two hours of further stirring at 80° C., neutralized with acetic acid, with the pH being monitored (see above) by means of previously moistened pH paper, and measured by means of $^1$H-NMR. The residual contents of unreacted aminosilane determined here are shown in Table 1.

Example 3

Process not According to the Invention for Preparing N-(3-tri-methoxysilylpropyl)-O-methylcarbamate The procedure of Example 1 is repeated, but this time a reaction temperature of 80° C. is set from the beginning, i.e. the aminopropyltrimethoxysilane is introduced at this temperature and the mixture is subsequently stirred further at this temperature for three hours.

The remainder of the experiment is carried out exactly as described in Example 1.

A pale yellow product which still contains considerable amounts of unreacted aminosilane (see Table 1) is obtained.

In this experiment, too, small samples (<5 ml) are taken during the reaction after a subsequent stirring time of one hour, two hours and three hours (end of the reaction), neutralized with acetic acid, with the pH being monitored (see above) by means of previously moistened pH paper, and measured by means of $^1$H-NMR. The residual contents of unreacted aminosilane determined here are shown in Table 1.

Example 5

Process not According to the Invention for Preparing N-(3-tri-methoxysilylpropyl)-O-methylcarbamate The procedure of Example 1 is repeated, but this time a reaction temperature of 55° C. is set from the beginning, i.e. the aminopropyltrimethoxysilane is introduced at this temperature and the mixture is subsequently stirred further at this temperature for three hours.

The remainder of the experiment is carried out exactly as described in Example 1.

A pale yellow product which still contains considerable amounts of unreacted aminosilane (see Table 1) is obtained.

In this experiment, too, small samples (<5 ml) are taken during the reaction after a subsequent stirring time of one hour, two hours and three hours (end of the reaction), neutralized with acetic acid, with the pH being monitored (see above) by means of previously moistened pH paper, and measured by means of $^1$H-NMR. The residual contents of unreacted aminosilane determined here are shown in Table 1.

Example 6

Process not According to the Invention for Preparing N-(3-Tri-Methoxysilylpropyl)-O-Methylcarbamate The procedure of Example 1 is repeated, but this time a reaction temperature of 40° C. is set from the beginning, i.e. the aminopropyltrimethoxysilane is introduced at this temperature and the mixture is subsequently stirred further at this temperature for three hours.

The remainder of the experiment is carried out exactly as described in Example 1.

A pale yellow product which still contains considerable amounts of unreacted aminosilane (see Table 1) is obtained.

In this experiment, too, small samples (<5 ml) are taken during the reaction after a subsequent stirring time of one hour, two hours and three hours (end of the reaction), neutralized with acetic acid, with the pH being monitored (see above) by means of previously moistened pH paper, and measured by means of $^1$H-NMR. The residual contents of unreacted aminosilane determined here are shown in Table 1.

Example 7

Process not According to the Invention for Preparing N-(3-tri-methoxysilylpropyl)-O-methylcarbamate The procedure of Example 2 is repeated, but this time a reaction temperature of 80° C. is set from the beginning, i.e. the dimethyl carbonate is introduced at this temperature and the mixture is subsequently stirred further at this temperature for three hours.

The remainder of the experiment is carried out exactly as described in Example 1.

A pale yellow product which still contains considerable amounts of unreacted aminosilane (see Table 1) is obtained.

In this experiment, too, small samples (<5 ml) are taken during the reaction after a subsequent stirring time of one hour, two hours and three hours (end of the reaction), neutralized with acetic acid, with the pH being monitored (see above) by means of previously moistened pH paper, and measured by means of $^1$H-NMR. The residual contents of unreacted aminosilane determined here are shown in Table 1.

Evaluation

The contents of unreacted 3-aminopropyltrimethoxysilane after the respective further stirring time are shown in Table 1.

TABLE 1

|  | Subsequent stirring time: 1 h | Subsequent stirring time: 2 h | Subsequent stirring time: 3 h |
|---|---|---|---|
| Example 1, Subsequent stirring conditions: 1 h at 55° C., 2 h at 80° | 15.2% | 0.0% | 0.0% |
| Example 2, Subsequent stirring conditions: 1 h at 55° C., 2 h at 80° | 5.6% | 0.0% | 0.0% |
| Example 3, Subsequent stirring conditions: 3 h at 80° C. * | 9.1% | 8.3% | 8.3% |
| Example 4, Subsequent stirring conditions: 3 h under reflux * | 51.2% | 45.9% | 41.1% |
| Example 5, Subsequent stirring conditions: 3 h at 55° C. * | 14.6% | 8.3% | 4.8% |
| Example 6, Subsequent stirring conditions: 3 h at 40° C. * | 20.6% | 14.5% | 10.0% |
| Example 7, Subsequent stirring conditions: 3 h at 80° C. * | 5.2% | 4.9% | 4.8% |

* not according to the invention

Example 8

Process According to the Invention for Preparing N-(3-tri-ethoxysilylpropyl)-O-ethylcarbamate A mixture of 522.7 g (1.781 mol) of aminopropyltriethoxysilane and 2.80 g of a 30% strength by weight solution of sodium ethoxide in ethanol (corresponds to 0.83 g of pure sodium ethoxide) is placed in a 2 l four-neck flask provided with dropping funnel, Liebig condenser, precision glass stirrer and thermometer and heated to 55° C. At this temperature, 252.6 g (2.138 mol) of diethyl carbonate are added over a period of 30 minutes. To maintain the temperature, slight cooling is necessary.

The mixture is subsequently stirred at 55° C. for a further two hours and is then heated to 80° C. At this temperature, the mixture is stirred for a further two hours.

Finally, 0.92 g of acetic acid are added. A drop taken from the reaction mixture is placed on a previously moistened pH paper. The reaction mixture displays a pH of 5.

The low boilers are removed from the neutralized reaction mixture by distillation. For this purpose, the pressure is reduced in steps to down to 1 mbar, while the temperature at the bottom firstly remains at 80° C. and is finally increased once again to 130° C. The distillation is concluded as soon as no more distillate goes over. Analysis of the distillate by means of GC and/or $^1$H-NMR shows that the distillate consists virtually exclusively (i.e. to an extent of more than 99%) of the ethanol liberated during the reaction and the diethyl carbonate which has been used in excess.

A pale yellow product is obtained in a purity of 97.9%. The residual content of the aminopropyltriethoxysilane used is 0.8%. The yield is very high (>97%) based on the aminosilane used.

The invention claimed is:

1. A process for preparing carbamatoorganosilanes of the formula (3),

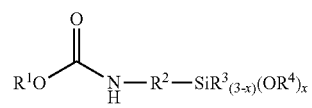

(3)

comprising reacting an aminoorganosilane of the formula (4), $$NH_2—R^2—SiR^3_{(3-x)}(OR^4)_x \quad (4)$$

with a dialkyl carbonate of the formula (5),

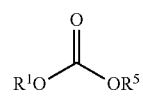

(5)

in the presence of a basic catalyst, where
 $R^1$, $R^3$, $R^4$ and $R^5$ are identical or different and are each a monovalent, unsubstituted or substituted hydrocarbon radical,
 $R^2$ is a divalent, unsubstituted or substituted hydrocarbon radical and
 x is 1, 2 or 3,
  and during the reaction there is a first reaction period in which the reaction temperature is in the range of from 35 to 65° C. for a time of at least 30 minutes and there is a later reaction period in which the reaction temperature is at least 10° C. higher than during the first reaction period.

2. The process of claim 1, where the radical $R^5$ is an unsubstituted monovalent hydrocarbon radical having from 1 to 6 carbon atoms.

3. The process of claim 1, wherein the radical $R^4$ is a substituted alkyl radical having from 1 to 4 carbon atoms.

4. The process of claim 1, wherein the radical $R^2$ is an unsubstituted alkylene radical having from 1 to 6 carbon atoms.

5. The process of claim 1, wherein the temperature during the first reaction period is from 45° C. to 65° C.

6. The process of claim 1, wherein the temperature during the later reaction period is at least 20° C. higher than in the first reaction period.

7. The process of claim 1, wherein the aminosilanes of the formula (4) and the dialkyl carbonates of the formula (5) are used in a mole ratio of from 1.0:1.0 to 1.0:2.0.

8. The process of claim 1, wherein a metal alkoxide is used as a catalyst.

9. The process of claim 1, wherein the content of the catalyst is not more than 0.2% by weight, based on the weight of the total reaction mixture.

10. The process of claim 1, wherein the content of unreacted aminoorganosilane present in the reaction mixture at the end of the reaction is less than 1 mol % based on the weights of aminoorganosiloxane and carbamatoorganosilane at the end of the reaction.

11. The process of claim 1, wherein the content of unreacted aminoorganosilane present in the reaction mixture at the end of the reaction is less than 0.5 mol % based on the weights of aminoorganosiloxane and carbamatoorganosilane at the end of the reaction.

12. The process of claim 1, wherein the content of unreacted aminoorganosilane present in the reaction mixture at the end of the reaction is less than 0.3 mol % based on the weights of aminoorganosiloxane and carbamatoorganosilane at the end of the reaction.

13. The process of claim 1, wherein the temperature of the first reaction period is between 50° C. to 65° C.

\* \* \* \* \*